(12) United States Patent
Silkaitis et al.

(10) Patent No.: US 10,458,992 B2
(45) Date of Patent: Oct. 29, 2019

(54) BREATH SAMPLING AND ANALYSIS DEVICE

(71) Applicants: Danius Silkaitis, Seattle, WA (US); Steven A. Rodriguez, Seattle, WA (US); David A. Herrin, Seattle, WA (US); Stephen M. Bailey, Shoreline, WA (US)

(72) Inventors: Danius Silkaitis, Seattle, WA (US); Steven A. Rodriguez, Seattle, WA (US); David A. Herrin, Seattle, WA (US); Stephen M. Bailey, Shoreline, WA (US)

(73) Assignee: GM Nameplate, Inc., Seattle, WA (US)

( * ) Notice: Subject to any disclaimer, the term of this patent is extended or adjusted under 35 U.S.C. 154(b) by 160 days.

(21) Appl. No.: 15/398,609

(22) Filed: Jan. 4, 2017

(65) Prior Publication Data

US 2017/0192008 A1 Jul. 6, 2017

Related U.S. Application Data

(60) Provisional application No. 62/274,708, filed on Jan. 4, 2016.

(51) Int. Cl.
*G01N 33/00* (2006.01)
*G01N 33/64* (2006.01)
(Continued)

(52) U.S. Cl.
CPC .......... *G01N 33/64* (2013.01); *A61B 5/0097* (2013.01); *A61B 5/082* (2013.01); *A61B 5/097* (2013.01);
(Continued)

(58) Field of Classification Search
CPC ................ G01N 33/497; G01N 33/64; G01N 2033/4975; G01N 2001/2244;
(Continued)

(56) References Cited

U.S. PATENT DOCUMENTS

2011/0021942 A1* 1/2011 Choe ...................... A61B 5/097 600/532
2011/0072883 A1* 3/2011 Abraham-Fuchs .... A61B 5/097 73/23.3

(Continued)

FOREIGN PATENT DOCUMENTS

EP 0 690 698 A1 1/1996

OTHER PUBLICATIONS

Extended European Search Report dated May 19, 2017, issued in corresponding European Application No. 17150294.1, filed Jan. 4, 2017, 8 pages.

*Primary Examiner* — Blake A Tankersley
(74) *Attorney, Agent, or Firm* — Christensen O'Connor Johnson Kindness PLLC

(57) ABSTRACT

A gas analysis device includes a canister with a cavity that is configured to receive a gas sample. A sensor is in fluid communication with the cavity and analyzes a portion of the gas sample that is received from the canister. The device also includes a blower assembly in fluid communication with the sensor. The blower assembly is configured to selectively draw a portion of the gas sample from the canister past the sensor so that the sensor is exposed to the portion of the gas sample.

20 Claims, 18 Drawing Sheets

(51) Int. Cl.
 *A61B 5/08* (2006.01)
 *G01N 33/497* (2006.01)
 *A61B 5/00* (2006.01)
 *A61B 5/097* (2006.01)
 *A61B 10/00* (2006.01)

(52) U.S. Cl.
 CPC .... *G01N 33/497* (2013.01); *A61B 2010/0087* (2013.01); *A61B 2505/07* (2013.01); *A61B 2560/0456* (2013.01); *G01N 2033/4975* (2013.01)

(58) Field of Classification Search
 CPC . A61B 2560/0456; A61B 5/082; A61B 5/097; A61B 2010/0087
 See application file for complete search history.

(56) References Cited

U.S. PATENT DOCUMENTS

| | | |
|---|---|---|
| 2013/0327122 A1 | 12/2013 | Dutta et al. |
| 2014/0276100 A1 | 9/2014 | Satterfield et al. |
| 2015/0289782 A1 | 10/2015 | Peverall et al. |
| 2017/0038355 A1* | 2/2017 | Fan .................... G01N 33/0073 |
| 2017/0160265 A1* | 6/2017 | Haick .................. G01N 33/497 |

* cited by examiner

BREATH SAMPLING AND ANALYSIS DEVICE

CROSS-REFERENCE TO RELATED APPLICATION

This application claims the benefit of U.S. Provisional Patent Application No. 62/274708, filed Jan. 4, 2016, which is incorporated herein by reference in its entirety.

BACKGROUND

Exhaled human breath typically comprises approximately 78% nitrogen, 15-18% oxygen, and 4-6% carbon dioxide. The remaining small fraction of exhaled breath generally consists of saturated water vapor and trace levels of more than 1000 volatile organic compounds (VOCs) with concentrations ranging from parts per trillion (pptv) to parts per million (ppmv).

The specific composition of a person's breath can indicate various health conditions. For example, acetone is a VOC in exhaled human breath that can indicate diabetes, heart disease, epilepsy, and other conditions. A person who is in a state of ketosis will have an increased breath concentration of acetone resulting from the body's production of ketone bodies. Acetone is also produced by ketosis resulting from a restricted calorie weight loss and/or exercise program. This acetone production is the result of metabolism of fat. Hence, a breath acetone content measurement can be used as an indication of a medical condition or of fat burning during a diet and/or program to show the effectiveness of the program.

Sensors such as those for detecting acetone in breath samples can be particularly sensitive to the manner in which the sensor is exposed to the sample being tested. While repeatable and accurate results can be obtained in a lab setting by exposing the sensors to a sample in a controlled manner, it is often desirable to analyze a breath sample outside of a lab setting.

Consumer devices and/or portable devices for testing breath samples are typically used outside of a controlled laboratory setting. Such devices generally take a live breath sample and expose the sensor directly to the exhaled human breath, resulting in readings that are neither repeatable nor accurate. Collecting live breath samples, particularly from multiple subjects, causes factors to vary that can otherwise be held relatively constant in the lab gas setup described above. These factors include velocity of exhaled breath, dynamic vapor pressure, duration of exhalation, total volume and individual size of exhaled droplets, and variable oxygen and acetone concentrations that are dependent on which part of the exhaled breath is sampled from (i.e. mouth air, deep lung air, or somewhere in between). Collectively and individually, these variables contribute to poor repeatability and inaccurate measurements.

Known sensors also suffer from designs that inhibit accuracy and repeatability, even when exposed to a controlled, consistent flow of a breath sample. One example of a known acetone sensor, includes tungsten trioxide ($WO_3$) disposed on an alumina or anodic aluminum oxide (AAO) substrate. This and similar sensors have typically been packaged in cylindrical leaded components, such as a standard TO-5 header 602. While TO-5 and similar headers are readily available, they are expensive, even at high manufacturing volumes. In addition, gas sensors housed in a TO type header are typically exposed to an air sample via diffusion, either through a mesh screen or a hole in the case. As a result, such sensors are typically not well-suited for applications involving a sample having a controlled mass flow.

Acetone sensors are useful for detecting various health conditions and/or for monitoring the efficacy of diet and exercise programs. The acetone level for diet and exercise is lower than that caused by diabetes. Accordingly, a more sensitive, accurate, and repeatable sensor is required in order to monitor increased acetone levels caused by diet and exercise. Exemplary embodiments of acetone sensors and their operation are disclosed in U.S. Patent Publication No. 2014/0366610, filed on Jun. 13, 2014, and U.S. Patent Application Publication No. 2014/0371619, filed Jun. 13, 2014, the disclosures of which are incorporated by reference.

The present disclosure is directed to a breath sampling and analysis system that captures a breath sample and provides it to a sensor in a manner that produces accurate and repeatable detection of various breath components. Although the described embodiment is directed toward the detection of acetone in a breath sample, it will be appreciated that alternate embodiments are possible wherein other sample components are sensed, and such embodiments should be considered within the scope of the present disclosure.

SUMMARY

A first representative embodiment of a gas analysis device according to the present disclosure includes a canister with a cavity that is configured to receive a gas sample. A sensor is in fluid communication with the cavity and analyzes a portion of the gas sample that is received from the canister. The device also includes a blower assembly in fluid communication with the sensor. The blower assembly is configured to selectively draw a portion of the gas sample from the canister past the sensor so that the sensor is exposed to the portion of the gas sample.

A second representative embodiment of a gas analysis device according to the present disclosure includes a valve and a canister in fluid communication with the valve. The valve is configured to receive a gas sample. The device further includes a filter configured to deliver filtered air to the valve. A blower assembly is also in fluid communication with the valve and is configured to draw fluid from the valve. A sensor, which is configured to sense a component of the gas sample, is exposed to a portion of the gas sample as the gas sample moves from the valve to the blower assembly. The valve is selectively moveable between a first position, in which the blower is in fluid communication with the canister, and a second position, in which the blower is in fluid communication with the filter.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Similarly, any steps described herein may be interchangeable with other steps, or combinations of steps, in order to achieve the same or substantially similar result. In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Prior to discussing the details of various aspects of the present disclosure, it should be understood that the following description includes sections that are presented largely in terms of logic and operations that may be performed by conventional electronic components. These electronic components may be grouped in a single location or distributed over a wide area, and can generally include processors, memory, storage devices, input/output circuitry, etc. It will be appreciated by one skilled in the art that the logic described herein may be implemented in a variety of configurations, including but not limited to, hardware, software, and combinations thereof. In circumstances were the components are distributed, the components are accessible to each other via communication links.

Figure 1:
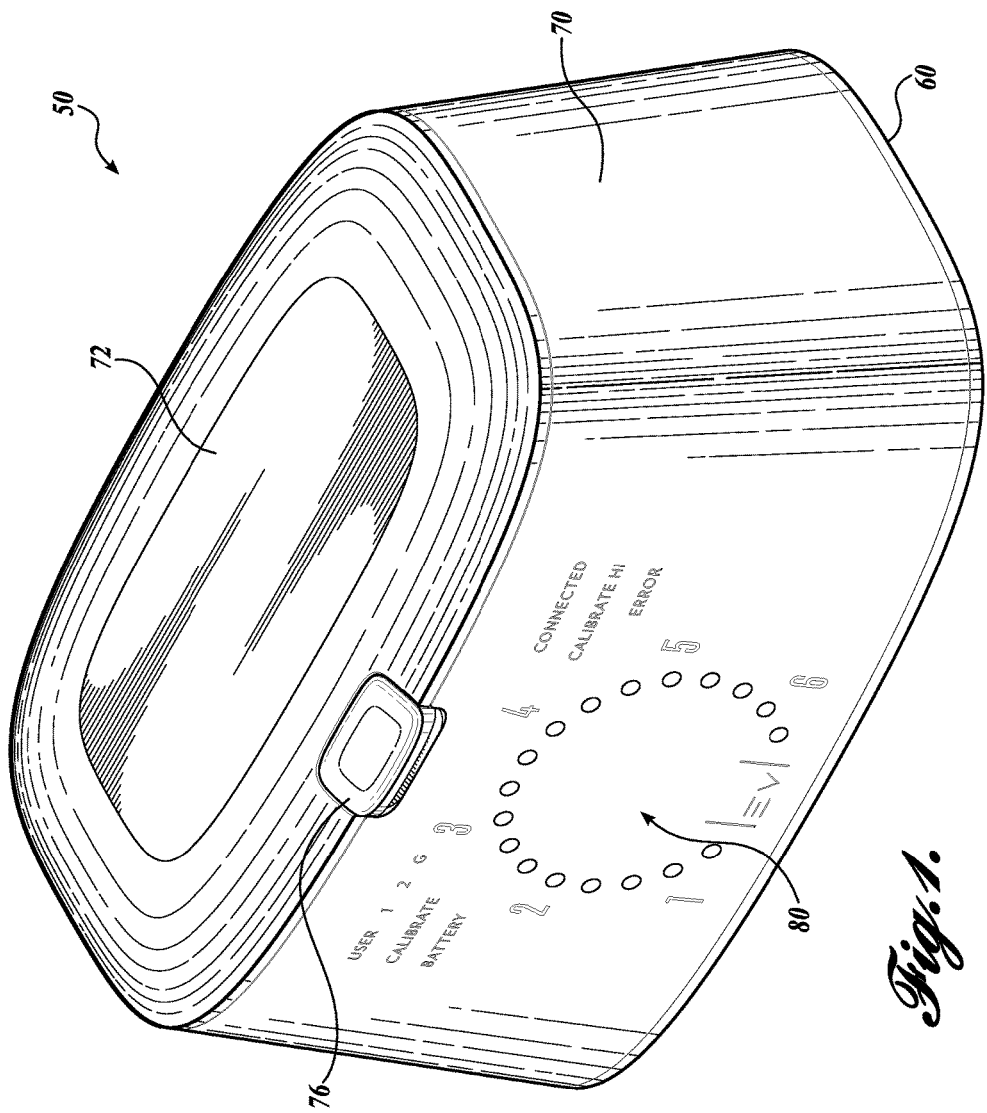
FIG. 1 shows a front top isometric view of a representative embodiment of a breath sampling and analysis device according to the present disclosure.
Figure 2:
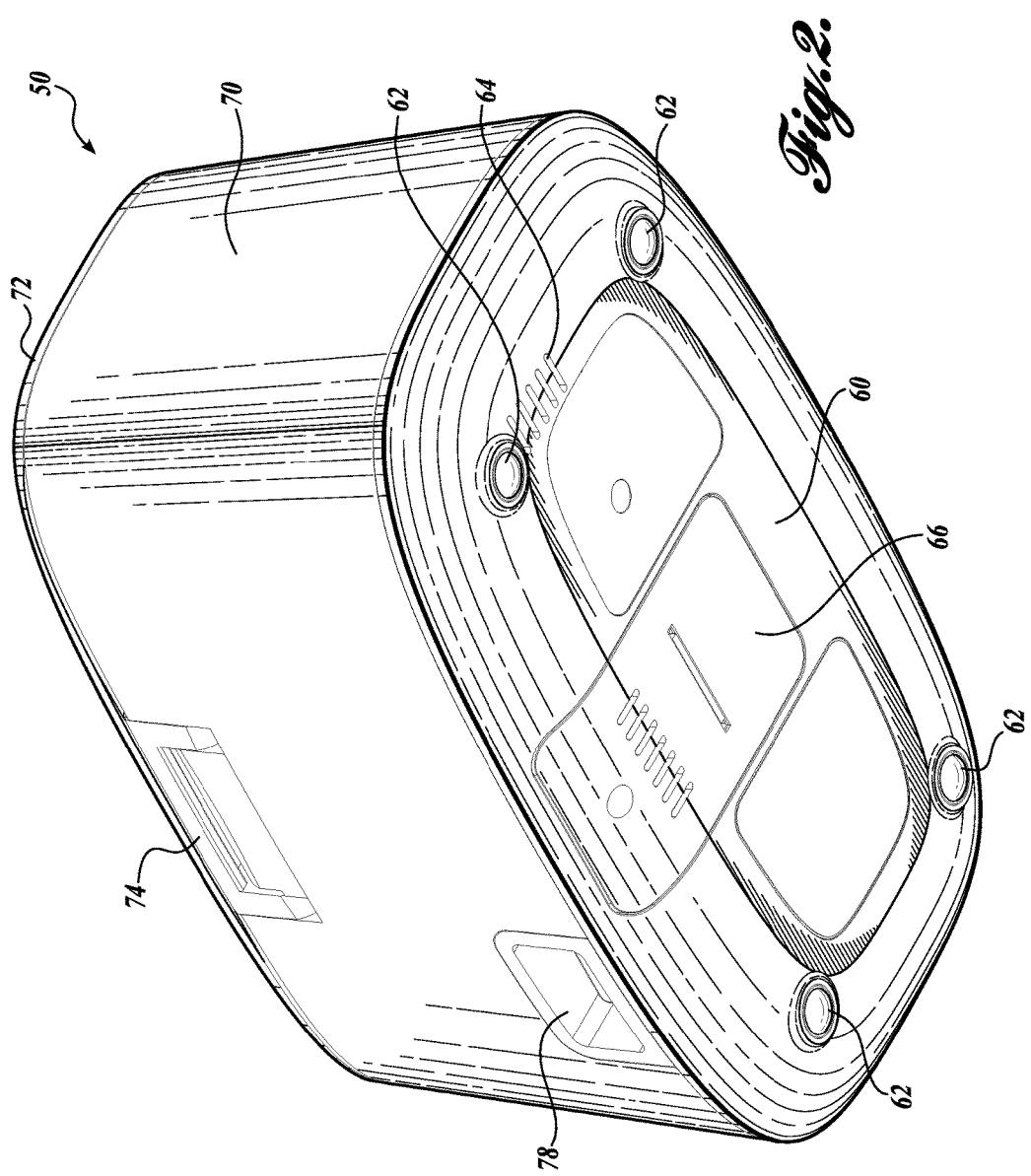
FIG. 2 shows a rear bottom isometric view of the breath sampling and analysis device shown in FIG. 1.

FIGS. 1 and 2 show a front-top isometric view and a rear-bottom isometric view, respectively, of a representative embodiment of a breath sampling and analysis device 50 according to the present disclosure. The device 50 includes base 60 with a housing 70 mounted thereto. The base 60 includes a plurality of feet 62 positioned on the bottom of the base to provide stability to the device 50 when placed on a surface. The feet 62 also elevate the bottom of the base 60 from the surface upon which the device 50 is placed in order to provide a path for airflow from vents 64 formed in the base. The base 60 also includes one or more access panels 66 to allow a user to access the internal components of the device 50.

A lid 72 is rotatably coupled to the top of the housing 70 by a hinge 74. The hinge 74 is preferably a spring loaded hinge that biases the lid 72 toward an open position. The device 50 further includes a latch 76 that selectively secures the lid 72 in a closed position. The housing 70 is sized and configure to contain the components of the device 50 and may provide an aesthetically pleasing appearance. The housing 70, base 60, and lid 72 cooperate to make the device 50 self-contained and easily portable.

A display 80 is located on a surface of the housing to provide information to a user regarding the operation of the device. In the illustrated embodiment, the display 80 comprises a plurality of lights that can be selectively illuminated to indicate operating conditions, such as whether the battery is charging, state of battery charge, readiness of the device to collect a breath sample, success of a breath sample collection, mode of operation, or any other information that would be desired by the user. The color, display duration, and pattern of the lights can be varied to indicate different conditions. Further, it will be appreciated that disclosed embodiment can incorporate any suitable type of displays and signals to relay information to a user, including LCD screens, LED screens, audible signals, haptic signals, or any other type of combination of displays and signals. It will be appreciated that the type of information displayed indicated on the display 80 can vary and is not limited to the disclosed embodiment. Further, the location and appearance of the display 80 can vary within the scope of the present disclosure.

Information can be conveyed from the device 50 to a user in a number of different ways. In addition to or in lieu of the illustrated display, the device can be connected to a personal computer, a network, a cell phone, or any other electronic device using a Wi-Fi, usb, Ethernet cables, Bluetooth, cellular communication, or any other suitable configuration.

Further, the information can be displayed as a visual indicator, an audio signal, a tactile response, or any other suitable method for communicating information to a user. In another contemplated embodiment, a processor/controller stores the data locally, or makes the data available for transfer to a remote storage location or processor, such as a home computer, tablet, smart phone, etc. These and other functions suitable for receiving, processing, storing, or displaying diagnostic data are contemplated and should be considered within the scope of the present disclosure.

Figure 3:
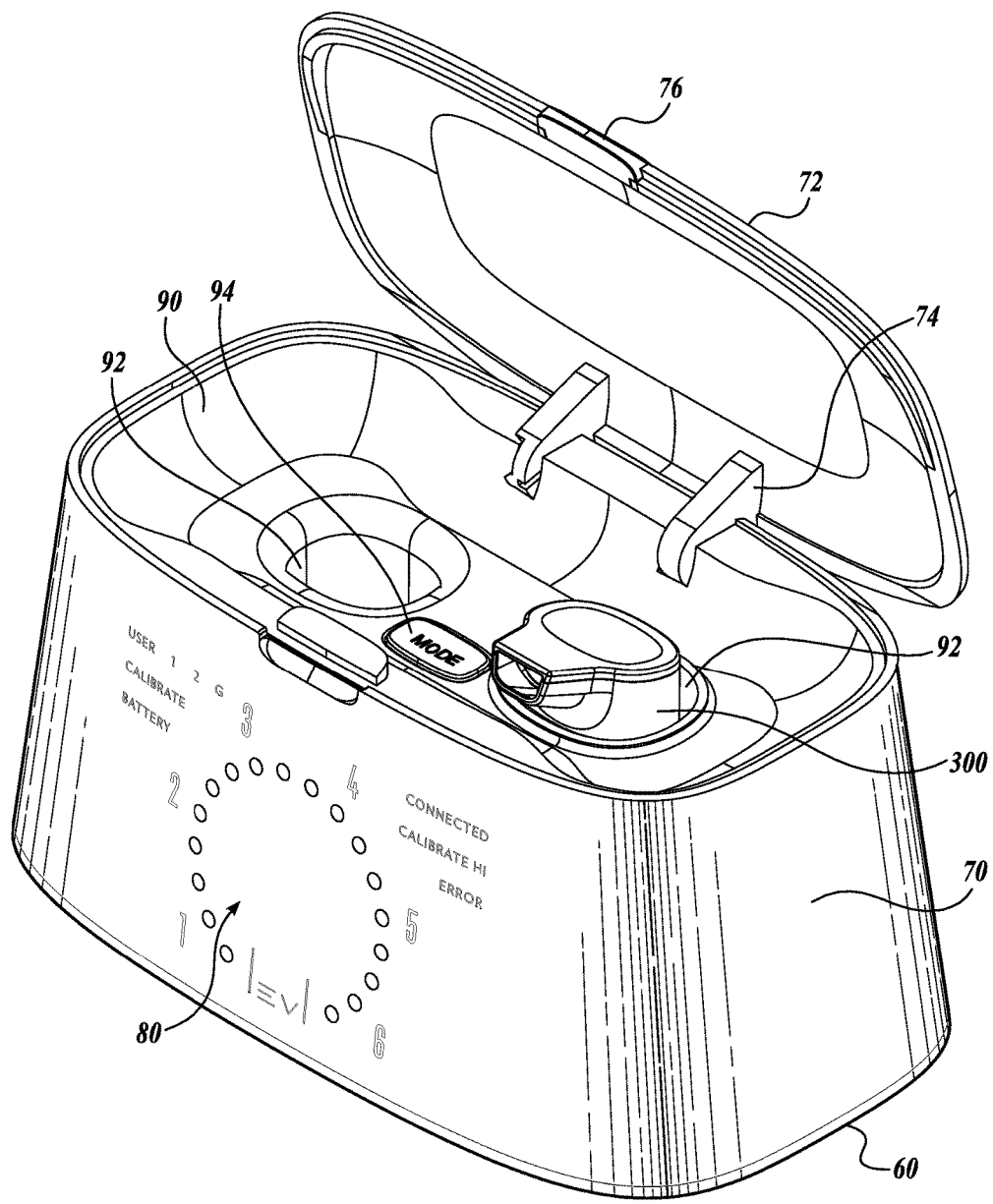
FIG. 3 shows a front top isometric view of the breath sampling and analysis device shown in FIG. 1 with a lid in the open position.
Figure 4:
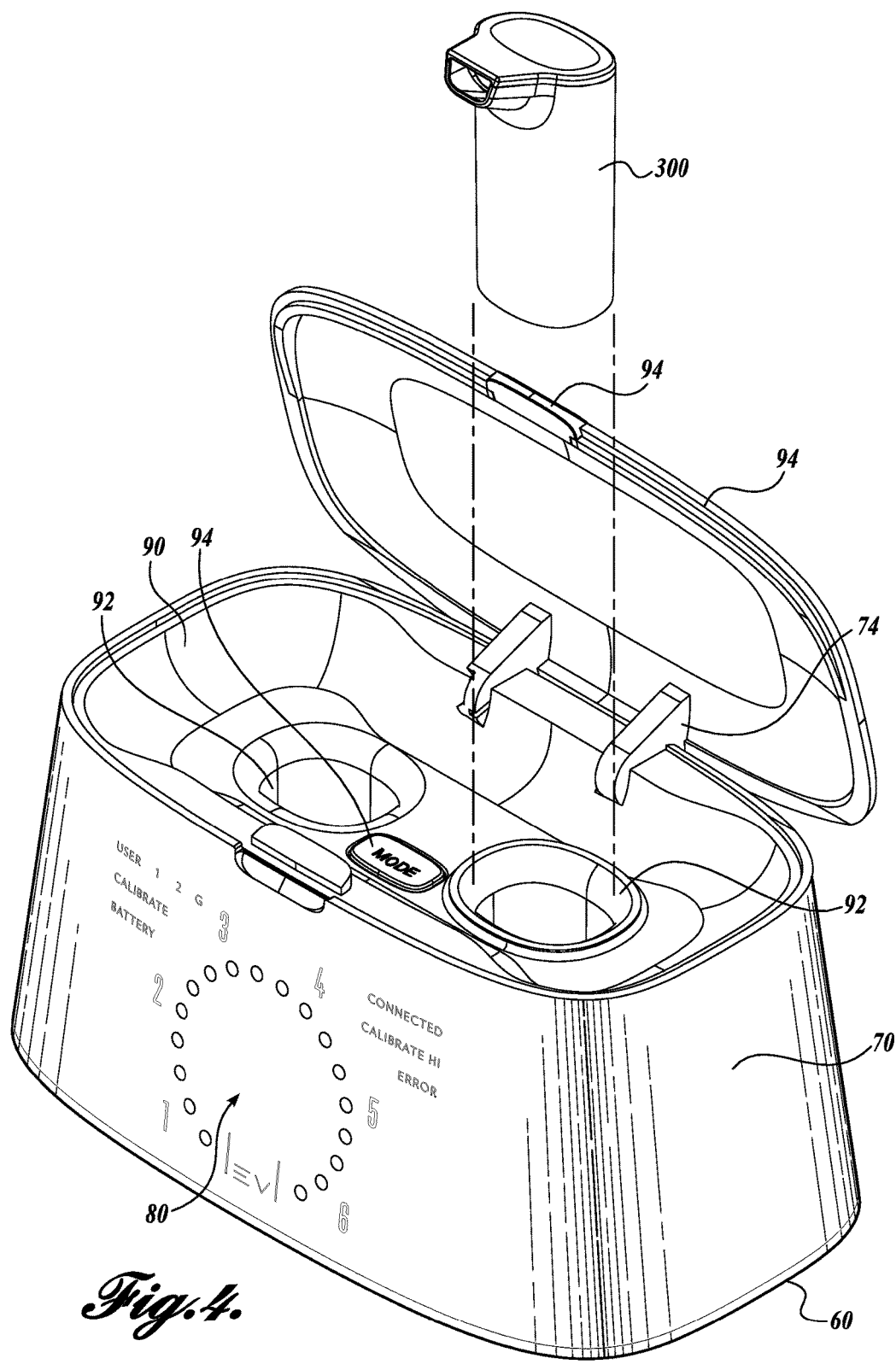
FIG. 4 shows a front top isometric view of the breath sampling and analysis device shown in FIG. 3 with a sample canister removed.
Figure 5:
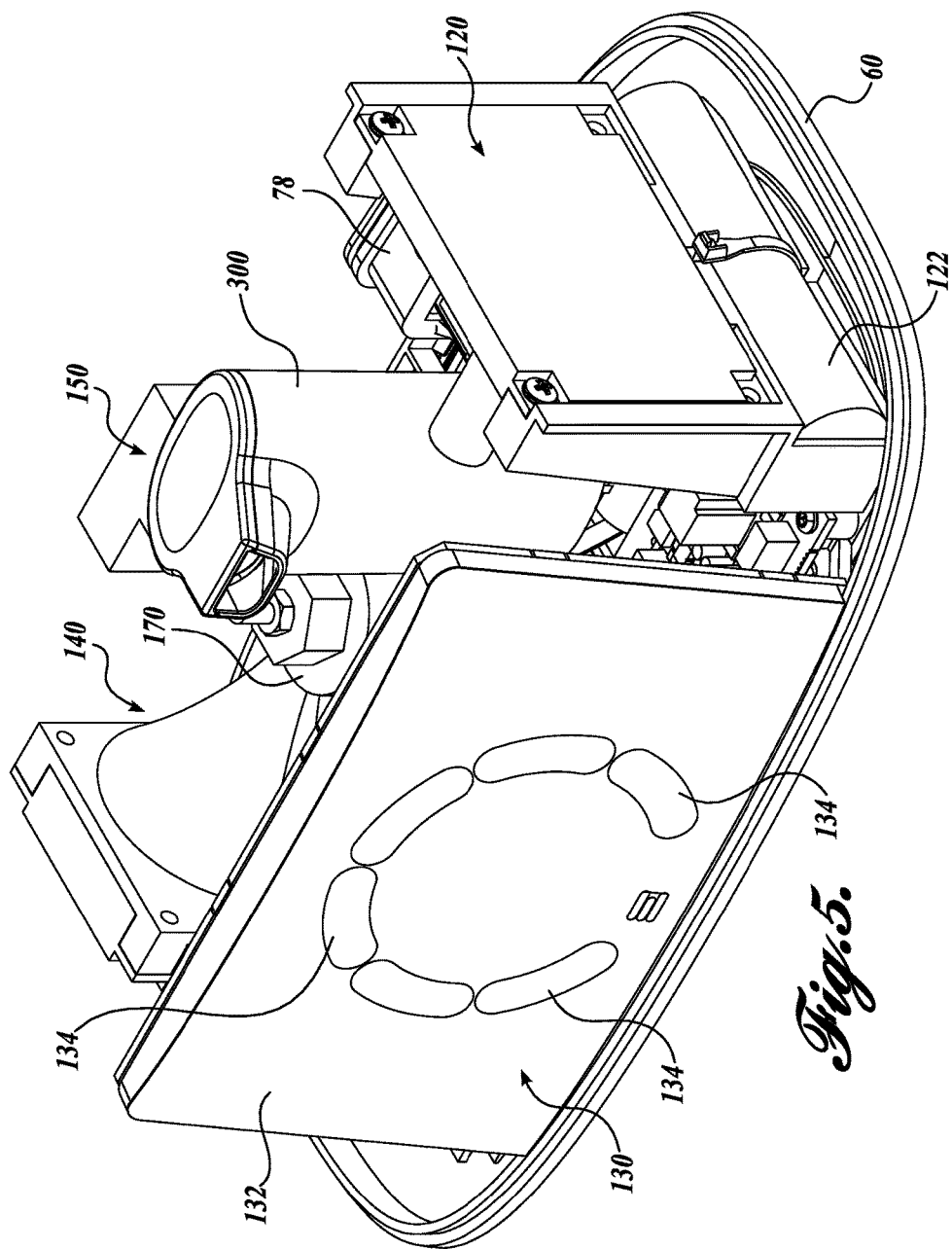
FIG. 5 shows a front top isometric view of the breath sampling and analysis device shown in FIG. 1 with a housing removed.
Figure 6:
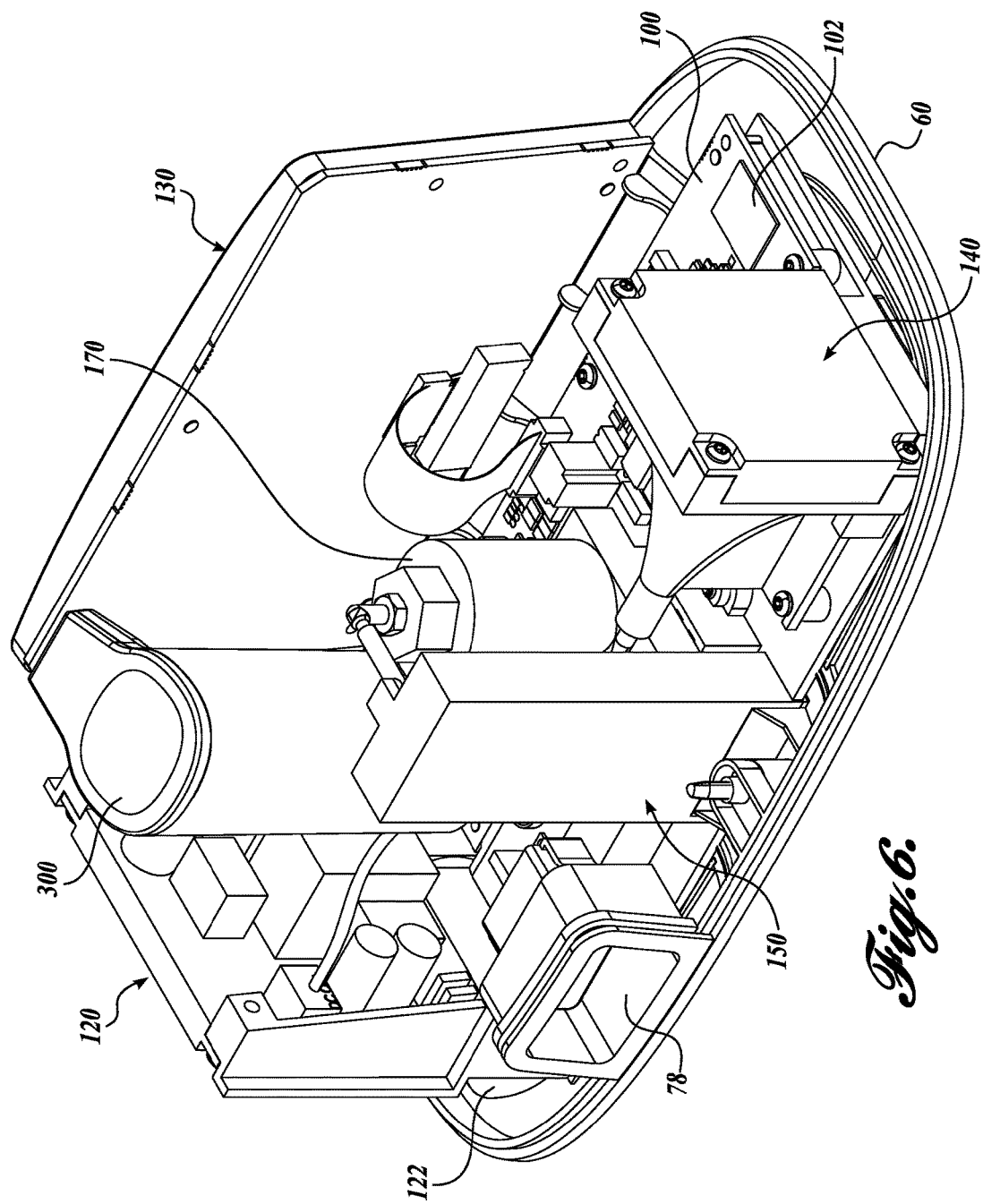
FIG. 6 shows a rear top isometric view of the breath sampling and analysis device shown in FIG. 5.
Figure 7:
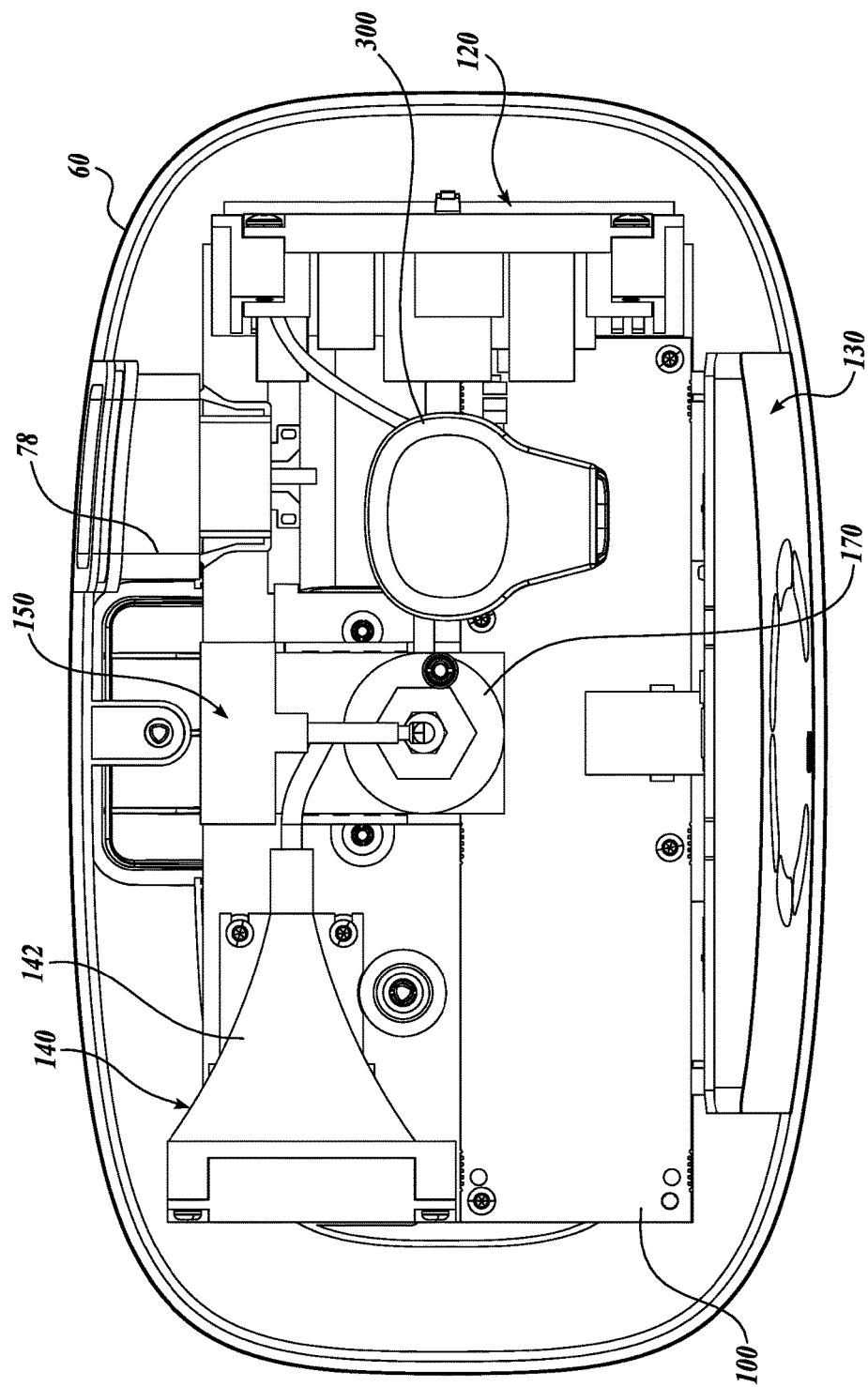
FIG. 7 shows a top view of the breath sampling and analysis device shown in FIG. 5.
Figure 8:
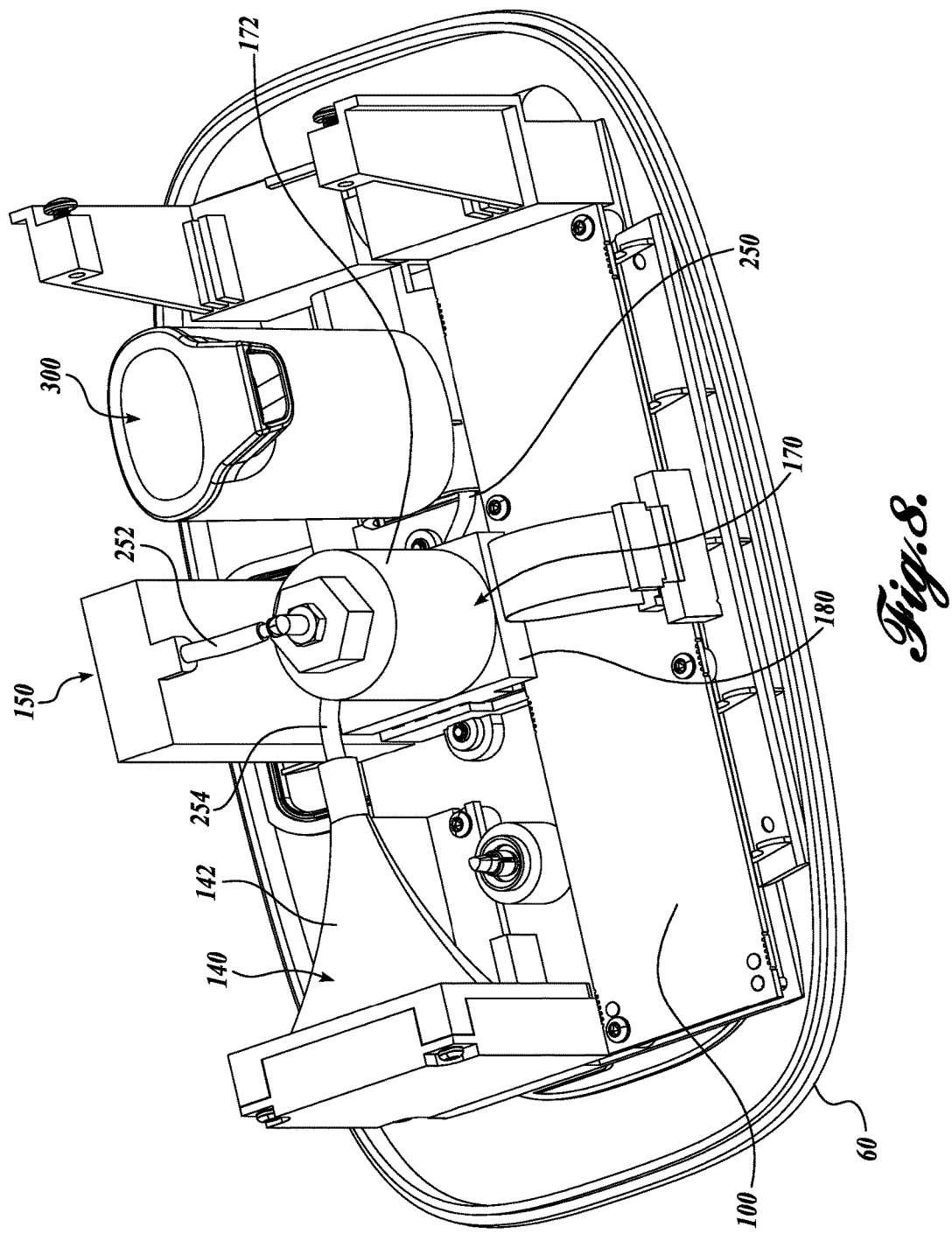
FIG. 8 shows a rear top isometric view of the breath sampling and analysis device shown in FIG. 1 with the housing and various components removed.
Figure 9:
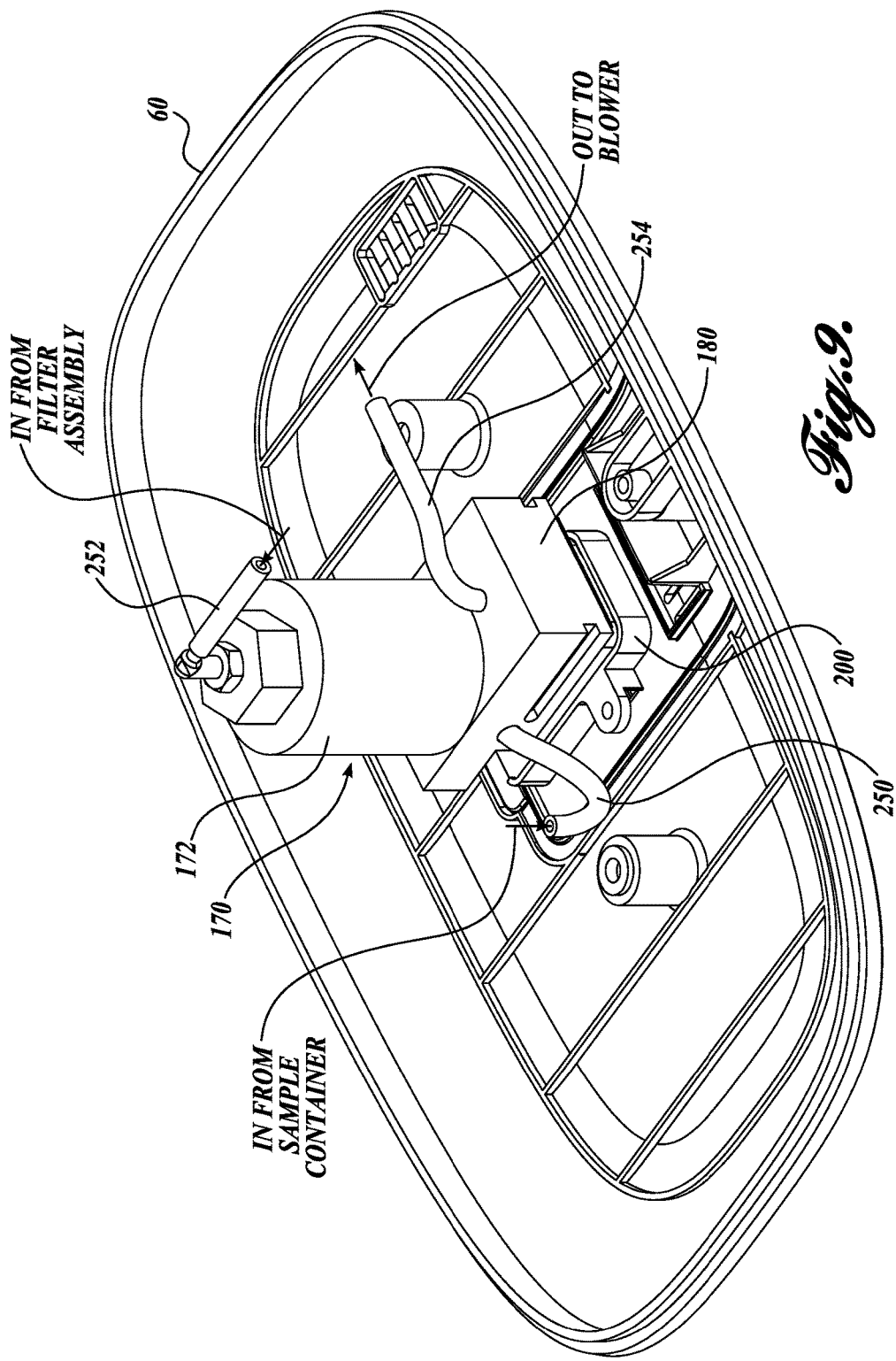
FIG. 9 shows a rear top isometric view of the breath sampling and analysis device shown in FIG. 8 with the additional components removed.

Referring now to FIGS. 3 and 4, a tray 90 is mounted to the upper end of the housing 70 and is disposed under the lid 76. The tray 90 extends across the top of the housing 70 and includes two apertures 92 sized and configured to receive a removable breath sample canister 300. One or more buttons 94 are located on the tray to allow a user to operate various features of the device 50. It will be appreciated that the number and location of buttons may vary and the disclosed embodiment should not be considered limiting. When the lid 76 is closed, the button 94, apertures 92 and sample canister 300 are not accessible. Thus, the lid 76 protects the canister 300 and prevents inadvertent activation of the device 50, while providing a clean, aesthetically pleasing appearance. When the lid 76 s open, the sample canister 300 can be removed from the device 50 and the button 94 is accessible to operate the device 50.

FIGS. 5-9 show the device 50 with the housing 70 and lid 76 removed. The internal components of the device 70 include a printed circuit board (PCB) 100 with a processor/controller 102 for controlling various aspects of the operation of the device 50. A power supply 120 is operably connected to the PCB 100 to provide power to the PCB and other device components. The power supply 120 includes an interconnection coupler 78, such as an ICE coupler, that allows a power cord to be utilized to provide power to the device 50. The power supply 120 also includes one or more batteries 122 to provide a power when the device 50 is unplugged.

An LED display 130 is mounted to the front of the base 60. The display includes a plurality of lighted areas 134 disposed on a panel 132. The lighted areas 134 correspond to translucent areas of the display 80. The controller 102 is operatively connected to the LED display 130 to selectively illuminate the various lighted areas 134. When a lighted area 134 is illuminated, the corresponding translucent area is illuminated to provide information to a user. The translucent areas can have the shape of words, numbers, symbols, or other shapes that are selectively illuminated by the LED display 130. In the illustrated embodiment, the display 80 includes words and a round meter comprising a plurality of smaller circles. During operation of the device 50, the controller 102 selectively illuminates different lighted areas 134 of the LED display 130 to provide information to the user. It will be appreciated that the display 80 is not limited to the illustrated embodiment. In this regard, any number of different translucent areas can be incorporated to provide different information to the user. Further, different types of displays, such as LED panels, LCD panels, or any other suitable displays, can be utilized and such displays should be considered within the scope of the present disclosure.

Still referring to FIGS. 5-9, the sample container 300 is in fluid communication with a three-way valve 170, which is itself in fluid communication with a blower assembly 140 and a filter assembly 150. In the illustrated embodiment, the valve 170 is a known three-way solenoid valve. That is, the valve 170 includes three connected passageways. A first passageway, which leads to the blower assembly 140, is always open. A second passageway and a third passageway are in fluid communication with the sample canister 300 and the filter assembly 150, respectively. A solenoid 172 selectively moves a plunger so that either the second or third passageway is blocked while the other passageway remains open and in fluid communication with the first passageway.

The valve 170 is operably coupled to the controller 102, which selectively moves the valve between a first position and a second position. In the first position ("the measurement position"), the valve 170 defines a measurement flow path in which (1) the blower assembly 140 is in fluid communication with the sample canister 300, and (2) flow between the blower assembly 140 and the filter assembly 150 is blocked. In the second position ("the purge position"), the valve 170 defines a purge flow path in which (1) the blower assembly 140 is in fluid communication with the filter assembly 150, and (2) flow between the blower assembly 140 and sample canister 300 is blocked.

Although the valve 170 is described as being a three-way solenoid valve, it will be appreciated that other valves may be utilized. In this regard, any suitable valve that can selectively reciprocate to alternately provide a measurement flow path and a purge flow path may be utilized, and the use of such alternate valves should be considered within the scope of the present disclosure.

The blower assembly 140 includes a fan (not shown) disposed within a bell-shaped housing 142. A tachometer is operatively coupled to the fan and sends signals to the processor 102 to indicate the speed of the fan. The housing 142 is connected at one end to the valve assembly 170 by a conduit 254. The blower assembly 140 is operatively coupled to the controller 102 so that the controller selectively controls not only when the blower assembly is running, but also the speed of the fan within the blower assembly. In operation, the controller 102 controls the blower assembly 140 so that the fan runs to create a reduced pressure on the valve side of the fan. That is, the blower assembly 140 draws gases from the valve 170. As will be described in further detail, the controller 102 also controls the speed of the fan so that the speed at which gases are drawn from the valve 170 corresponds to the device's mode of operation at a particular time.

Figure 10:
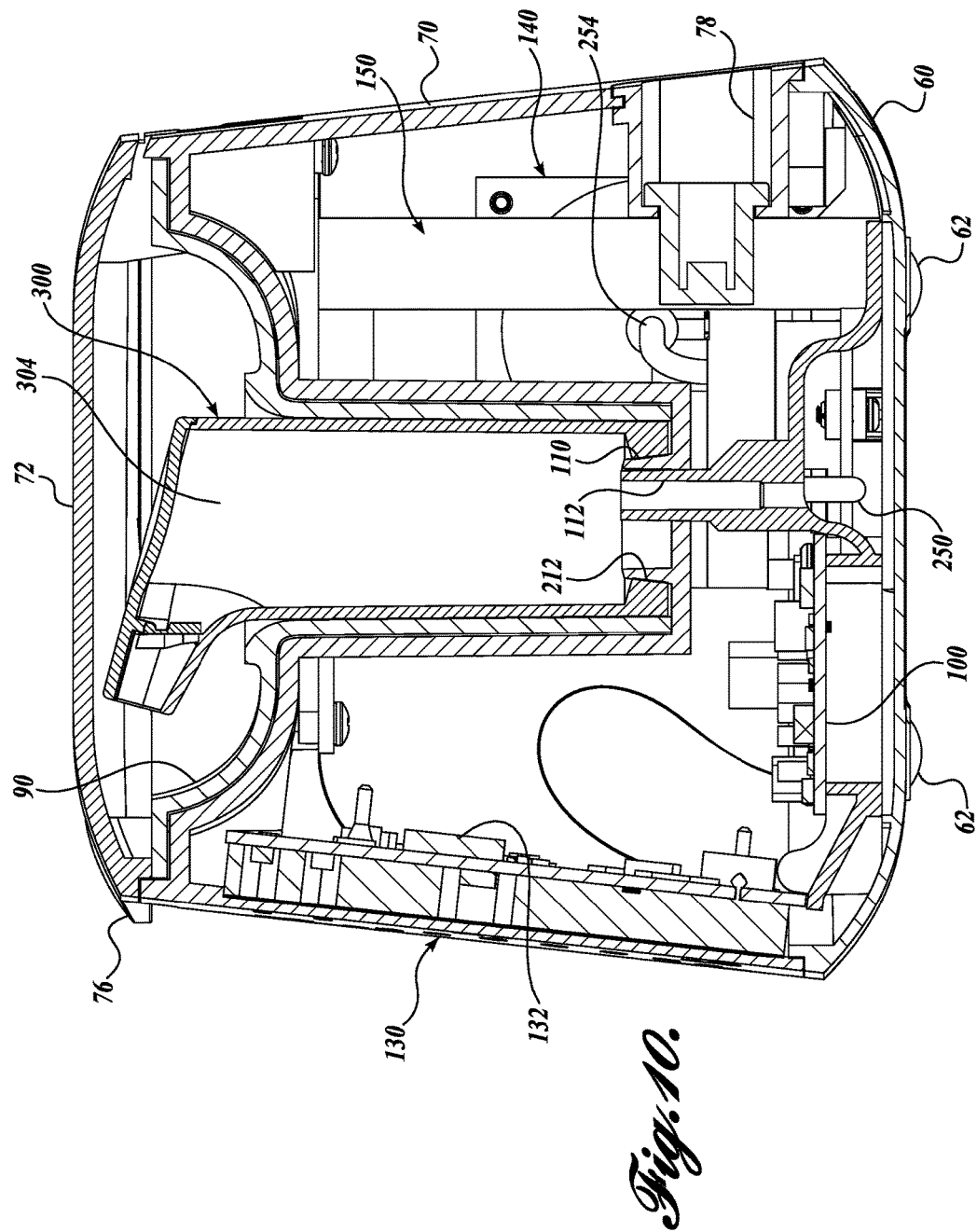
FIG. 10 shows a side cross-sectional view of breath sampling and analysis device shown in FIG. 1.
Figure 11:
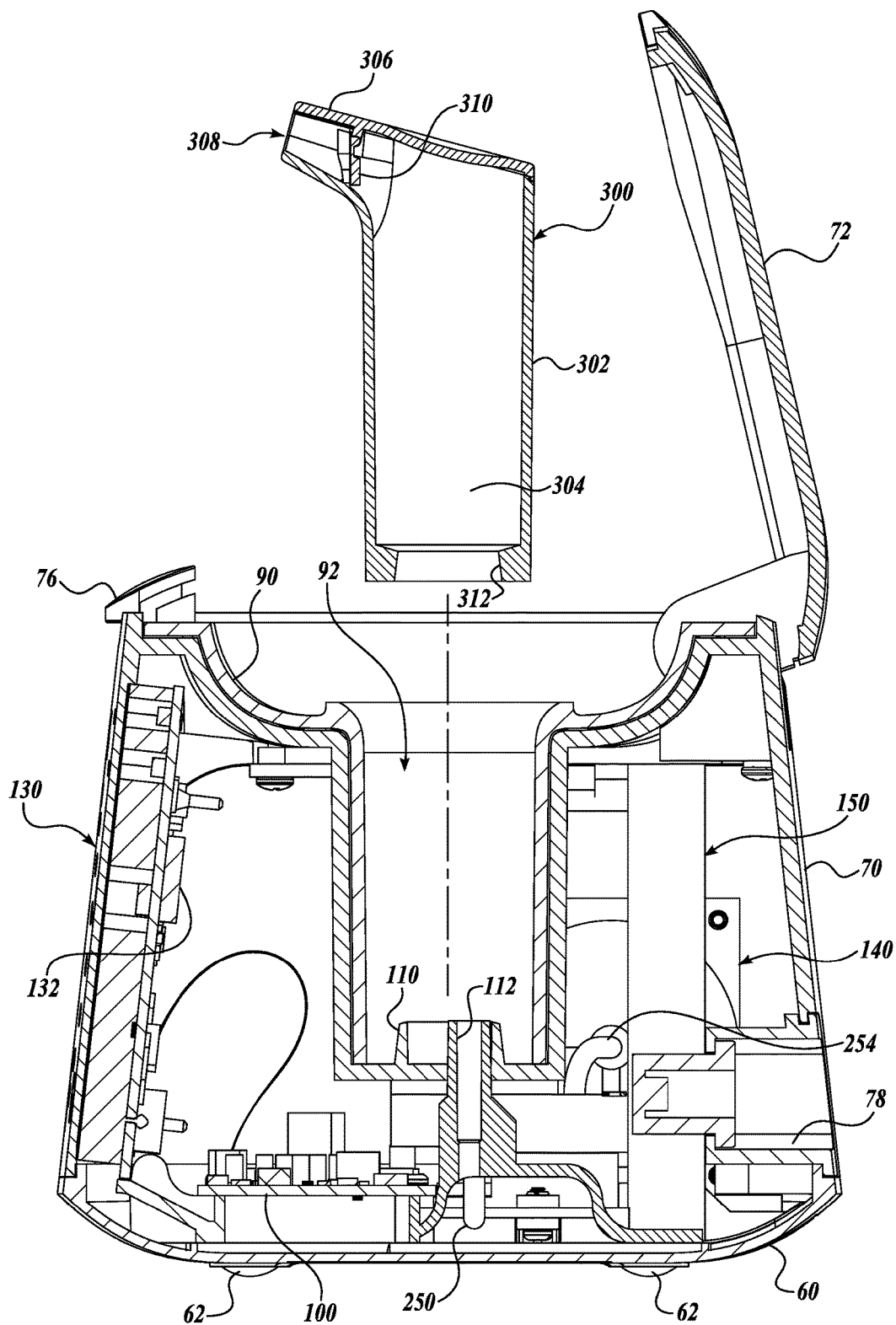
FIG. 11 shows a side cross-sectional view of breath sampling and analysis device shown in FIG. 10 with the sample canister removed.
Figure 12:
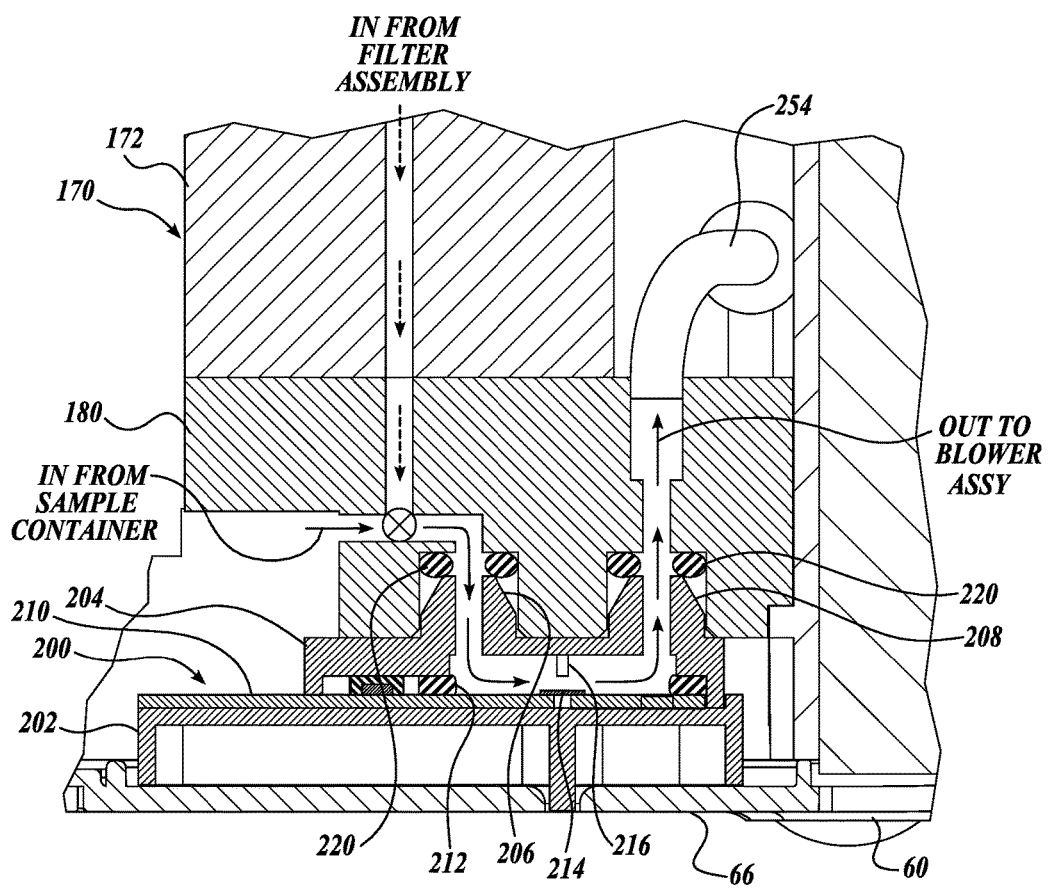
FIG. 12 shows a partial cross-sectional view of a valve and a sensor assembly of the breath sampling and analysis device shown in FIG. 1.
Figure 13:
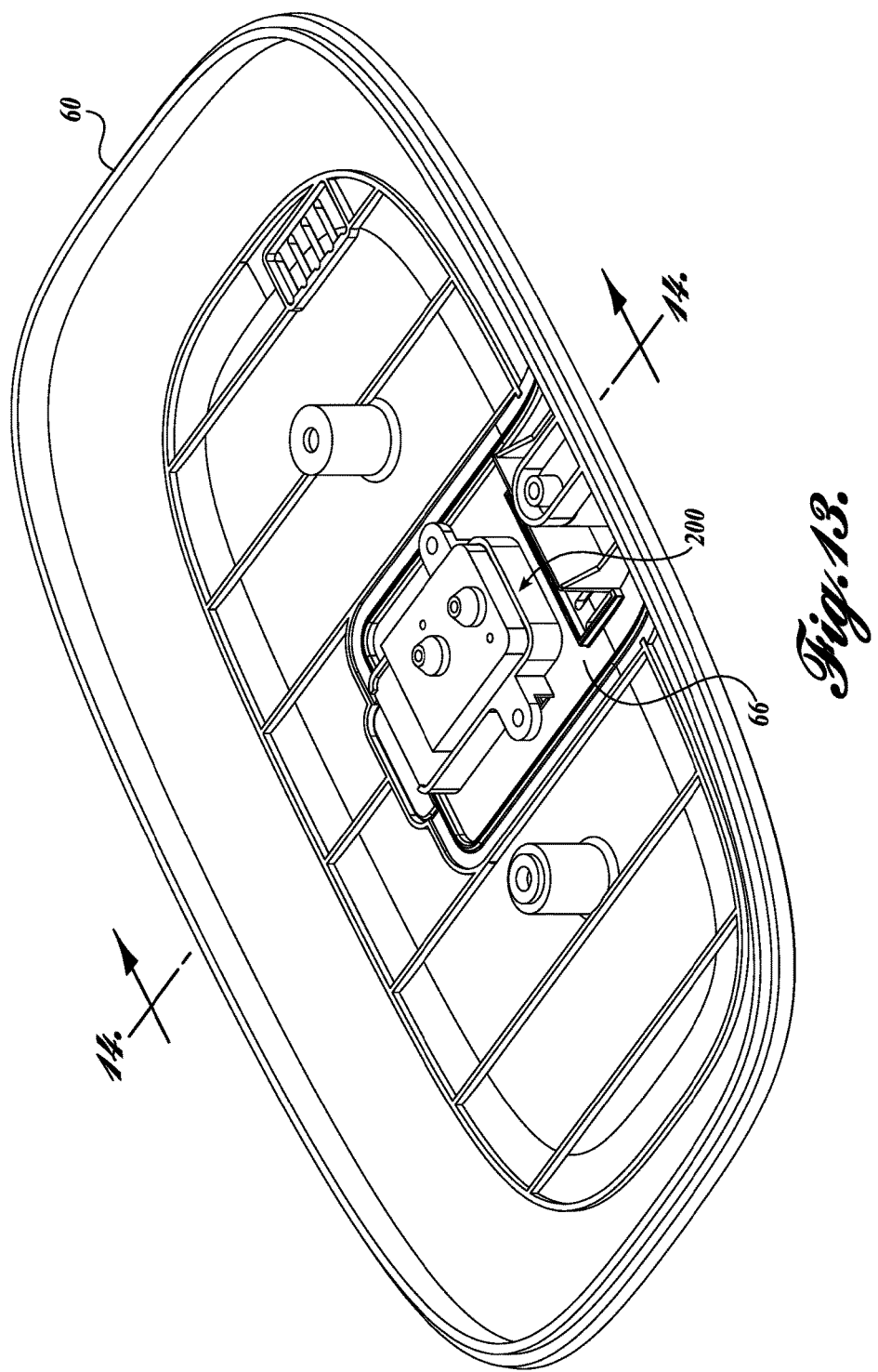
FIG. 13 shows a rear top isometric view of the a base and a sensor assembly of the breath sampling and analysis device shown in FIG. 12.
Figure 14:
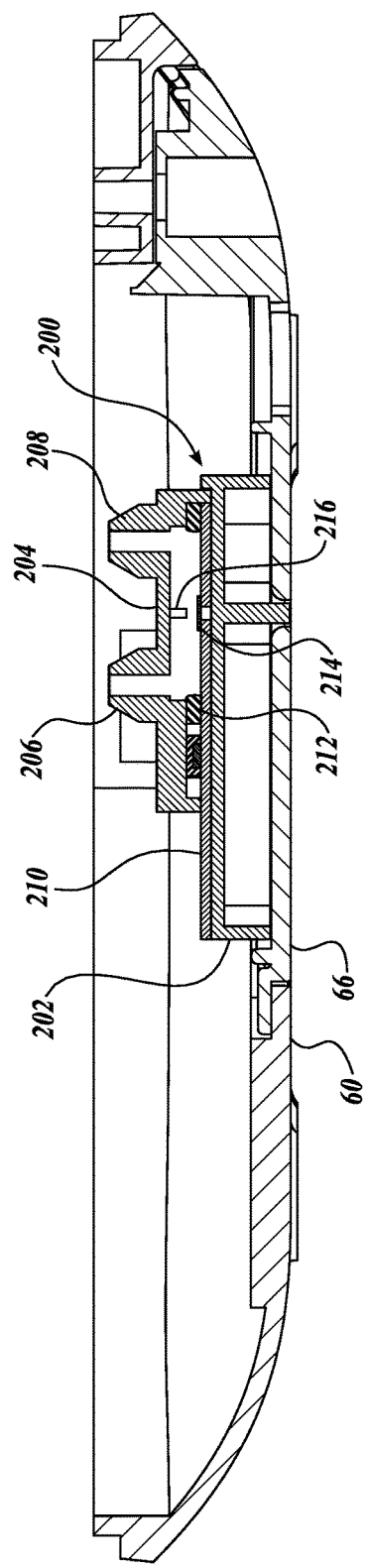
FIG. 14 shows a partial cross-sectional view of the base and the sensor assembly shown in FIG. 13.
Figure 15:
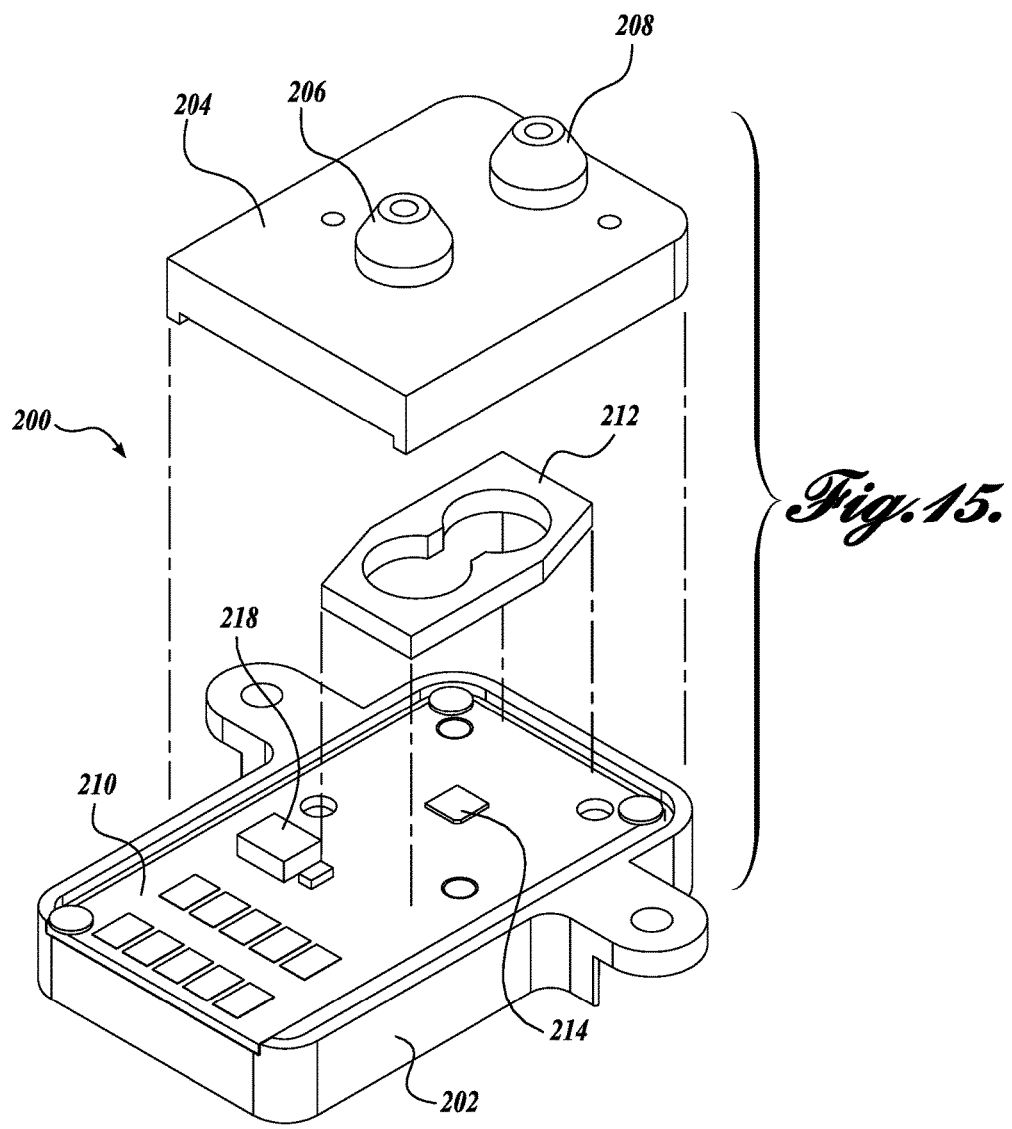
FIG. 15 shows an exploded isometric view of the sensor assembly shown in FIG. 13.

FIGS. 10 and 11 shown a cross-sectional view of the sample container 300 inserted into and removed from, respectively, the slot 92 of the device 50. The canister 300 has a generally cylindrical body 302 with an internal cavity 304. A mouthpiece 306 is formed at an upper end of the container 300 and has an inlet 308 in fluid communication with the cavity. A second aperture 312 is formed in a bottom end of the sample container 300. The mouthpiece 306 is sized and configured for a user to place the mouthpiece in his or her mouth and exhale a breath sample through the aperture 308 into the cavity. A flap 310 forms a one way valve 310 in the mouthpiece such that the flap allows a breath sample to enter the cavity 304, but prevents or minimizes the flow of the breath sample back out through the aperture 308.

Extending upward from the bottom of the slot 92 is a protrusion 110 sized to be received by the second aperture 312 of the breath sample canister 300. A channel 112 extends through the protrusion 110. When the sample canister 300 is placed in the slot 92, the protrusion 110 engages the second aperture 312 of the canister so that a first end of the channel 112 is in fluid communication with the interior cavity 304 of the canister. A second end of the channel 112 is connected to the valve 170 by a conduit 250 so that when the canister 300 is inserted in the slot 92, the interior cavity 304 of the canister is in fluid communication with the valve. As a result, when the valve 170 is in the measurement position, the interior cavity 304 of the container 300 is in fluid communication with the blower assembly 140.

Referring back to FIGS. 5-9, the filter assembly 150 includes a filter housing 152 that contains a filter medium (not shown). In one contemplated embodiment, the filter medium is an activated carbon foam that filters out particulate matter, VOCs, and other contaminates and interferents from air passed through the medium. It is contemplated that any number of suitable filter media may be utilized and such media should be considered within the scope of the present disclosure. One side of the filter housing 152 is connected to the valve 170 by a conduit 252. A second side of the filter housing 152 includes one or more apertures that provide a pathway for ambient air into the filter housing. When the valve 170 is in the purge position, the filter assembly 150 provides filtered ambient air to the blower assembly 140 through the valve 170.

Referring now to FIGS. 12-15, the valve 170 includes a manifold 180 that directs gases received from the sample canister 300 and the filter assembly 150 through a sensor module 200 before being discharged to the blower assembly 140. The illustrated embodiment of a sensor module 200 includes a printed circuit board 210 (PCB) disposed between a housing base 202 and a housing cover 204. The PCB 210 of the sensor module 200 is operably coupled to the main PCB 100 of the device 50 so that the sensor module 200 can send signals to and receive signals from the PCB 100. Moreover, the controller 102 can control the operation of the sensor module 200.

An inlet 206 and an outlet 208 are formed in the housing cover 204. The inlet 206 receives gases from the manifold 180, and the outlet 208 discharges the gases back into the manifold before they are discharged from the manifold to the blower assembly 140. In the illustrated embodiment, the inlet 206 and outlet 208 are frustoconical protrusions that engage openings in the manifold 180. O-rings 220 are disposed between the manifold 180 and the inlet 206 and outlet 208 to provide a seal between the manifold and the inlet and outlet.

A guide 212 is disposed between and cooperates with the housing base 202 and the housing cover 204 to define a path between the inlet 206 and the outlet 208 of the sensor module. An acetone sensor 214 is mounted to the PCB 210 so that the sensor spans the path. A tab 216 extends down from the housing cover 204 over the sensor 214 to direct gases flowing through the sensor module 200 toward the sensor 214. As the gas received from the blower assembly 140 or the sample canister 300 moves toward the blower assembly 140, it enters the inlet 206 of the sensor module 200, passes over the sensor 214, and then exits the outlet 208 toward the blower module.

In the illustrated embodiment, the sensor 214 is flat tungsten trioxide ($WO_3$) disposed on an alumina or anodic aluminum oxide (AAO) substrate. The described sensor 214 is suitable for detecting acetone in a breath sample; however, it is contemplated that other sensors suitable for sensing acetone may also be used. Further, sensors useful for sensing the presence, level, or other characteristics of other sample components may be utilized, and such sensors should be considered within the scope of the present disclosure.

A memory chip 218 is optionally mounted to the PCB 210. In the illustrated embodiment, the memory chip 218 is an EEPROM that is programmed with sensor 214 parameters, authentication data, and other information to be communicated with the controller 102. It will be appreciated that any number of other components may be mounted to the PCB 210 to provide functionality to the sensor module 200 and the breath sampling and analysis device 50 as a whole.

Known sensors are susceptible to a buildup of contaminants and/or interferents that can negatively impact the accuracy of the sensor. Thus, a sensor module 200 that is easily replaceable by a user provides an advantage over known sensors. In the illustrated embodiment, the sensor module 200 is mounted to an access door 66 using threaded fasteners or other suitable configurations. When the access door 66, which is positioned on the base 60 of the device 50, is in the closed position, the sensor module 200 engages contacts that operatively connect the sensor module with the PCB 100. When the access door 66 is opened, the sensor module 200 disengages the contacts. When the access door 66 is so positioned, the sensor module 200 can be demounted from the access door by removing the fasteners that secure the sensor module to the access door. A new sensor module 200 can then be mounted to the access door 66. When the access door 66 is closed, the new sensor module 200 engages the contacts to operatively connect the new module to the PCB 100.

Figure 16:
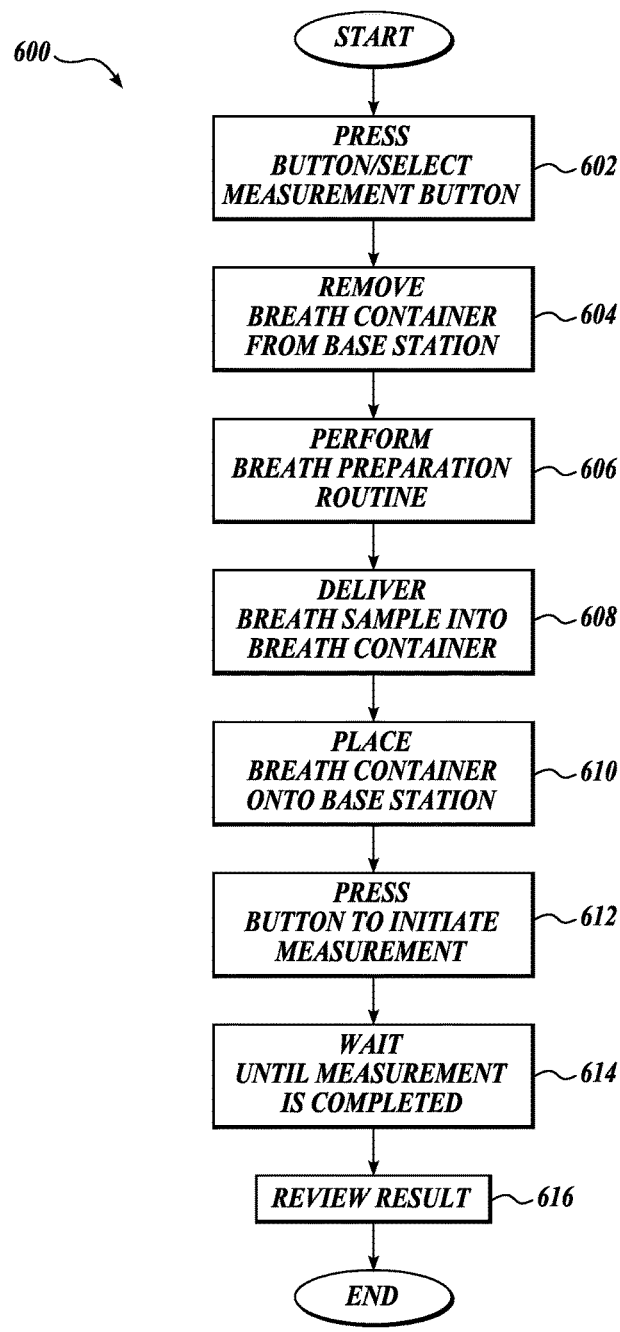
FIG. 16 shows a representative method for capturing and analyzing a breath sample.

The described breath sampling and analysis device 50 is suitable for a user to measure breath acetone levels. A representative method 600 for a user to operate the disclosed breath sampling and analysis device 50 is shown in FIG. 16. To start the method 600, a user proceeds to step 602 and presses the control button 94 to power up the device and ready the sensor 50 for operation.

Moving on to step 604, the user removes the breath sample canister 300 from the device 50. The method 600 then proceeds to step 606, in which the user performs a breath preparation routine to ensure that the breath sample is "deep lung air," which provides more accurate and repeatable measurements. An exemplary breath preparation routine may include taking a deep breath and holding the breath in for 5 to 10 seconds.

With the breath preparation routine completed, the method 600 moves on to step 608, in which the user delivers a breath sample to the breath sample canister 300 by breathing into the mouthpiece 306 for a period of 5 to 10 seconds. For the illustrated canister 300, the sample passes by the flap 310, which acts as a one-way check valve, into the cavity 304 of the canister. As the user continues to breath into the mouthpiece 306, excess breath exits the canister 300 through the canister outlet 312.

With a breath sample contained within the canister 300, method 600 moves to step 610, in which the user places the canister 300 into the slot 92, i.e., returns the canister to the base station. The method 600 then proceeds to step 612, in which the user presses the control button 94 to initiate a measurement.

In step 614, the user waits for the measurement to be completed by the device, after which the method 600 proceeds to step 616, in which the user reviews the results of the measurement. The method 600 ends after step 616.

Figure 17:
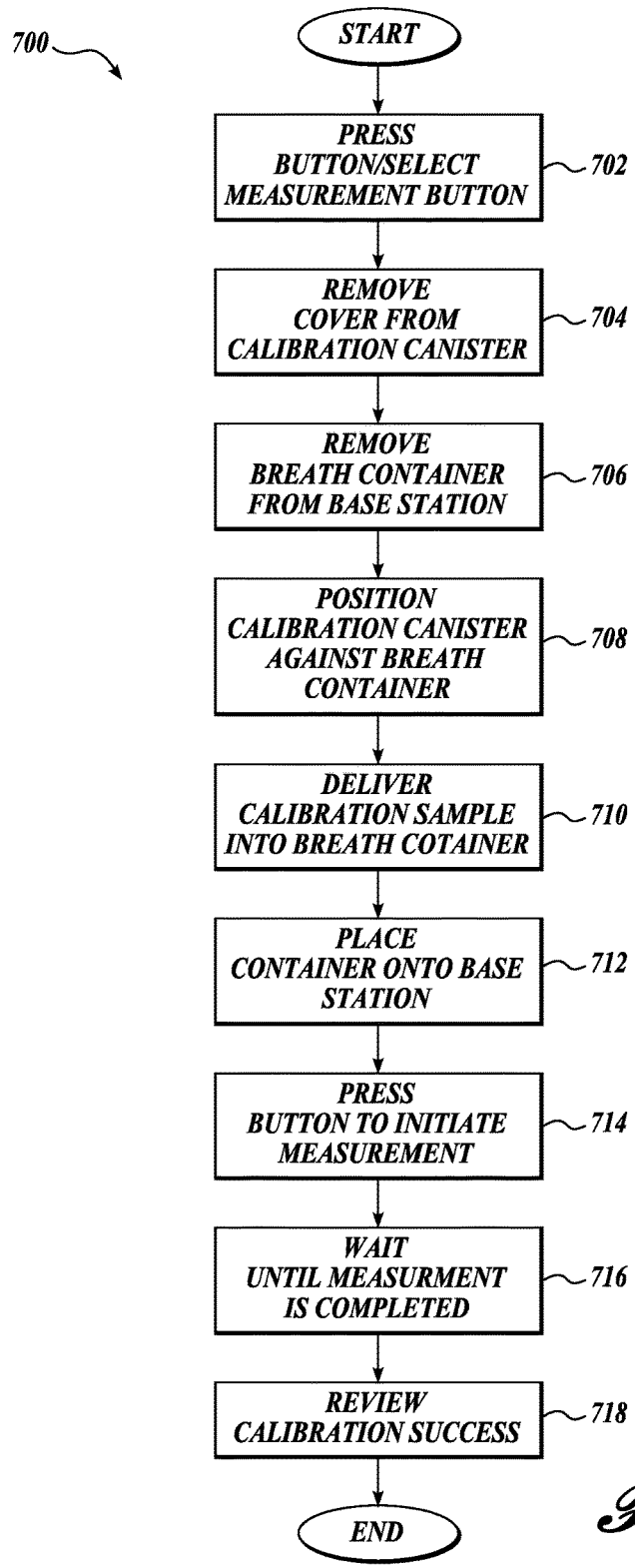
FIG. 17 shows a representative method for calibrating a breath analysis device.

In order to ensure accurate readings, it is necessary to perform an initial calibration of the sensor 214 and thereafter periodically perform additional calibrations. To facilitate calibration by a user, one representative embodiment of a calibration method utilizes an aerosol container ("a calibration container") filled with simulated breath sample having a known acetone level. FIG. 17 shows a representative method 700 for calibrating the sensor 214 of the described device 50. Starting at step 702, a user presses the control button 94 to place the device 50 in calibration mode.

Proceeding to step 704, the user removes the cover of the calibration container, and in step 706, removes the breath sample canister 300 from the device 50. Proceeding to step 708, the user positions the calibration container next to the breath sample canister 300, and in step 710, the user delivers the calibration sample into the breath sample canister 300.

The method 700 them proceeds to step 712, in which the user returns the breath sample canister 300 to the slot 92. In step 714, the user presses the control button 94 to initiate the calibration measurement. During the calibration measurement, the device 50 measures the acetone content of the calibration sample. Because the acetone content of the calibration sample is known, the device 50 senses an acetone content and then calibrates the device so that the sensed acetone content corresponds to the known, i.e., actual, acetone content.

In step 716, a user waits for the calibration measurement to be completed, and in step 718, the user reviews the results of the calibration to confirm that the calibration was successful.

Figure 18:
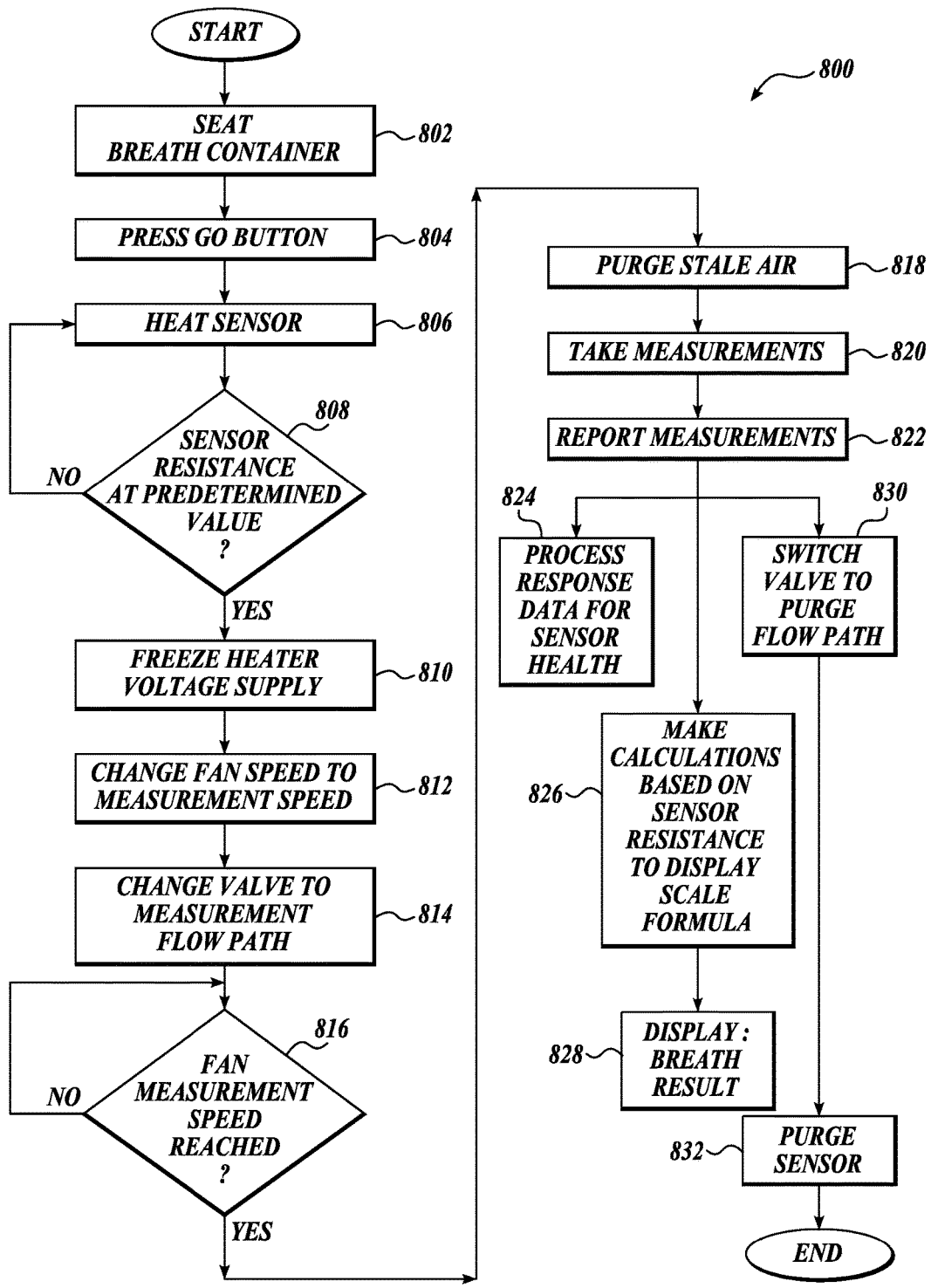
FIG. 18 shows a representative method for analyzing a breath sample.

FIG. 18 illustrates a representative method 800 performed by the device 50 during a breath sample measurement. The method 800 starts at step 802 when the sample canister 300 is inserted into the slot 92. The method proceeds to step 804 in which the user presses the control button 94 to start the measurement.

Because sensor readings vary with the sensor temperature, it is preferable for the sensor temperature, to be maintained at a predetermined level during a measurement sequence. As the sensor is measuring a breath component, the power to the sensor remains constant, and the resistance of the sensor changes according to the amount of acetone in the sample. Accordingly, maintaining sensor at a constant sensor temperature prevents inaccuracies due to resistance changes cause by temperature changes. In steps 806 and 808, the controller 102 heats the sensor 214 until the sensor resistance reaches a predetermined value. In step 810, the heater voltage supply is frozen to maintain the sensor resistance at the predetermined level.

In step 812, the fan speed of the blower assembly 140 is set to a measurement speed. In step 814, the valve 170 is set to the measurement flow path, wherein the blower assembly 140 is in fluid communication with the sample canister 300. The method 800 then proceeds to step 816 in which the speed of the fan is determined. The method remains at step 816 until the fan measurement speed is reached. By waiting to proceed until the fan measurement speed is reached, the method 800 ensures that the breath sample will pass through the sensor module 200 at a rate suitable for an accurate measurement.

With the fans measurement speed reached, the method 800 proceeds to step 818 for a predetermined amount of time to purge stale air from the device 50. With the stale air purged, the amount of acetone in the breath sample is measured by the sensor module 200 in step 820. In step 822, the sensed measurements are relayed to the controller 102.

The method proceeds to step 824, wherein the controller processes data from the sensor module 200 to evaluate the performance of the sensor 214. When certain criteria are met, the device signals a user that the sensor module 200 should be replaced.

In step 826, the controller calculates the breath analysis results, and in step 828, the device displays the results.

From step 822, the method 800 also proceeds to step 830, during which the valve 170 is switched from the measurement flow path to the purge flow path. With the valve 70 switched to the purge flow path, the method 800 proceeds to step 832, and the sensor is purged of the breath sample.

While illustrative embodiments have been illustrated and described, it will be appreciated that various changes can be made therein without departing from the spirit and scope of the invention.

The embodiments of the invention in which an exclusive property or privilege is claimed are defined as follows:

1. A gas analysis device, comprising:
   (a) a canister comprising a cavity, an inlet aperture, and an outlet aperture, wherein the canister is configured to receive a gas sample into the cavity through the inlet aperture, and wherein a cross-sectional area of the outlet aperture is smaller than a cross-sectional area of the cavity;
   (b) a sensor in fluid communication with the cavity and configured to analyze a portion of the gas sample received from the cavity;
   (c) a blower assembly in fluid communication with the sensor and configured to selectively draw the portion of the gas sample from the cavity through the outlet aperture to expose the sensor to the portion of the gas sample.

2. The device of claim 1, further comprising a valve disposed between the sensor and the canister, the valve being configured to selectively block fluid communication between the canister and the sensor.

3. The device of claim 2, further comprising a purge gas source in fluid communication with the valve, wherein the valve is selectively moveable between a first position, in which the sensor is in fluid communication with the canister, and a second position, in which the sensor is in fluid communication with the purge gas source.

4. The device of claim 3, wherein the blower assembly draws a purge gas from the purge gas source through the sensor when the valve is in the second position.

5. The device of claim 4, wherein fluid communication between the sensor and the purge gas source is blocked when the valve is in the first position, and fluid communication between the sensor and the canister is blocked when the valve is in the second position.

6. The device of claim 1, wherein the canister further comprises a one-way valve limiting flow of the gas sample out of the cavity through the inlet aperture.

7. The device of claim 4, wherein the sensor senses a component of the gas sample, and the purge gas comprises ambient air filtered by a filter assembly.

8. The device of claim 7, wherein the component is acetone.

9. The device of claim 7, further comprising a processor programmed to calculate an amount of the detected component.

10. The device of claim 1, wherein the canister is removable from a portion of the device.

11. The device of claim 10, wherein the gas sample is a breath sample, and the canister has a mouthpiece configured to receive the breath sample from a user.

12. A gas analysis device, comprising:
   (a) a valve;
   (b) a canister comprising a cavity, an inlet aperture, and an outlet aperture, the canister being in fluid communication with the valve and configured to receive a gas sample through the inlet aperture, a cross-sectional area of the outlet aperture being smaller than a cross-sectional are of the cavity;
   (c) a filter configured to deliver filtered air to the valve;

(d) a blower assembly in fluid communication with the valve and configured to draw fluid from the valve; and (e) a sensor configured to sense a component of the gas sample, wherein the sensor is exposed to a portion of the gas sample as the gas sample moves from the valve to the blower assembly, and wherein the valve is selectively moveable between a first position, in which the blower is in fluid communication with the outlet aperture of the canister, and a second position, in which the blower is in fluid communication with the filter.

13. The device of claim 12, wherein the valve is a three-way valve that selectively blocks fluid communication between the blower assembly and the canister, and between the blower assembly and the filter.

14. The device of claim 12, wherein the blower assembly draws filtered air from the filter when the valve is in the second position.

15. The device of claim 12, wherein the canister further comprises a one-way valve limiting flow of the gas sample out of the cavity through the inlet aperture.

16. The device of claim 12, wherein the gas sample is a breath sample, and the canister has a mouthpiece configured to receive the breath sample from a user.

17. The device of claim 12, wherein the filter comprises a filter housing and a filter medium disposed within the filter housing, wherein the blower assembly draws air from the filter when the valve is in the second position.

18. The device of claim 17, wherein the sensor senses a breath component, and the filter medium filters the breath component from ambient air.

19. The device of claim 18, wherein the breath component is acetone.

20. The device of claim 18, further comprising a processor programmed to calculate an amount of the detected breath component.

* * * * *

UNITED STATES PATENT AND TRADEMARK OFFICE
CERTIFICATE OF CORRECTION

PATENT NO. : 10,458,992 B2
APPLICATION NO. : 15/398609
DATED : October 29, 2019
INVENTOR(S) : Silkaitis et al.

Page 1 of 1

It is certified that error appears in the above-identified patent and that said Letters Patent is hereby corrected as shown below:

In the Claims

| Column | Line | |
|---|---|---|
| 10 (Claim 12, Line 8) | 66 | "are" should read --area-- |

Signed and Sealed this
Fifth Day of May, 2020

Andrei Iancu
*Director of the United States Patent and Trademark Office*